United States Patent [19]

Jackson et al.

[11] Patent Number: 5,516,443
[45] Date of Patent: May 14, 1996

[54] COMPOUNDS AND FUEL COMPOSITIONS

[75] Inventors: Graham Jackson, Reading; Rachel E. M. Kenward, Faringdon, both of United Kingdom

[73] Assignee: Exxon Chemical Patents Inc., Linden, N.J.

[21] Appl. No.: 196,083

[22] PCT Filed: Aug. 21, 1992

[86] PCT No.: PCT/EP92/01924

§ 371 Date: Feb. 18, 1994

§ 102(e) Date: Feb. 18, 1994

[87] PCT Pub. No.: WO93/04148

PCT Pub. Date: Mar. 4, 1993

[30] Foreign Application Priority Data

Aug. 22, 1991 [GB] United Kingdom .................. 9118105

[51] Int. Cl.⁶ ........................... C10M 133/04; C10L 1/22
[52] U.S. Cl. ................... 252/50; 44/424; 44/425
[58] Field of Search ............... 44/424, 425; 252/50; 564/336, 374

[56] References Cited

U.S. PATENT DOCUMENTS

| | | | |
|---|---|---|---|
| 2,613,208 | 10/1952 | Van Hook et al. | 260/247 |
| 2,696,427 | 12/1954 | Biswell | 44/424 |
| 3,388,103 | 6/1968 | Imöhl et al. | 564/375 |
| 3,402,200 | 9/1968 | Hayes | 44/425 |
| 3,474,143 | 10/1969 | Butte, Jr. | 252/50 |
| 3,598,782 | 8/1971 | Beckman et al. | 260/45.9 |
| 3,804,762 | 4/1974 | Jervis et al. | 252/50 |
| 4,034,040 | 7/1977 | Cronin et al. | 564/374 |
| 4,396,517 | 8/1983 | Gemmill, Jr. et al. | 252/51.5 R |
| 4,491,455 | 1/1985 | Ishizaki et al. | 44/62 |

FOREIGN PATENT DOCUMENTS

| | | |
|---|---|---|
| 182940 | 6/1985 | European Pat. Off. |
| 203693 | 12/1986 | European Pat. Off. |
| 1173280 | 3/1957 | France |
| 2258848 | 11/1974 | France |
| WO88/02394 | 4/1988 | WIPO |
| WO92/01924 | 8/1991 | WIPO |
| WO93/04148 | 3/1993 | WIPO |

OTHER PUBLICATIONS

PCT Preliminary Examination Report, PCT/EP92/01924, Exxon Chemical Patents, Inc. et al (Month N/A).
PCT International Search Report, PCT/EP92/01924, Exxon Chemical Patents, Inc. et al (Month N/A).

*Primary Examiner*—Ellen M. McAvoy
*Attorney, Agent, or Firm*—John J. Mahon

[57] ABSTRACT

A novel compound comprises a chemical compound comprising or including a cyclic ring system such as an aromatic ring system, the compound carrying at least two substituents of the general formula (I) below on the ring system

$$-A-NR^1R^2 \qquad (I)$$

where A is an aliphatic hydrocarbyl group that is optionally interrupted by one or more hetero atoms and that is straight chain or branched, and $R^1$ and $R^2$ are the same or different and each is independently a hydrocarbyl group containing 9 to 40 carbon atoms, optionally interrupted by one or more hetero atoms, the substituents being the same or different and the compound optionally being in the form of a salt thereof.

Such compounds may be used as additives for improving the cold flow properties of crude oil, lubricating oil or fuel oil.

17 Claims, 1 Drawing Sheet

COMPOUNDS AND FUEL COMPOSITIONS

This invention relates to chemical compounds and their use in improving the cold flow properties of crude oil, lubricating oil or fuel oil, for example distillate petroleum fuel such as middle distillate fuel oil boiling within the range of 110° C. to 500° C.

When oils and fuel oils are subjected to low ambient temperatures, wax may separate out from the fuel and impair the flow properties of the oil. For example, middle distillate fuels contain wax which precipitates at low temperatures to form large waxy; crystals which tend to plug the small pore openings of fuel filters. This problem is particularly acute when the fuel is a diesel fuel because the nominal apertures in the fuel filter of diesel engines are typically of diameter between about 5 and 50 microns.

U.S. Pat. No. 4,402,708 (Oswald; Exxon) describes a tetraalkyl phthalamide of the formula wherein $R^1$, $R^2$, $R^4$ and $R^5$ are $C_{16}$–$C_{40}$ straight chain alkyl groups and may be the same or different, and their use as additives or as co-additives, e.g. as synergists, in combination with wax crystal modifiers for controlling the size of wax crystals that form in a distillate fuel oil at low temperatures, and for inhibiting agglomeration of the wax crystals.

EP-A-0 203 81 2 (Exxon) describes an additive composition suitable for improving low temperature flow properties of a wax-containing petroleum distillate fuel comprising a tetraalkyl phthalamide such as described above; an ethylene polymer and/or copolymer; a condensation product of a halogenated paraffin or an olefin with an aromatic compound; and an alkylated ether.

U.S. Pat. No. 3 598 782 (Beckman et al; Firestone) describes the use of $N,N,N^1,N^1$-tetra-substituted xylylenediamines as their mixed para- and meta-derivatives as stabilisers for unvulcanised rubbery interconnected stereolinear polymers. The substituents are generically stated to include alkyl groups of 1 to 20 carbon atoms, methyl, ethyl and isopropyl being mentioned but not specifically exemplified.

GB-A-1 464 510 (Pfizer) describes the use of N,N-dialkylxylenediamines in combating virus infections, the alkyl groups generically being stated to contain from 12 to 20 carbon atoms and specific examples being the ortho and para derivatives where the alkyl groups are n-hexadecyl.

This inveniion relates to a novel group of tetra hydrocarbyl derivatives, each hydrocarbyl group having a defined chain length and their use as additives for improving the cold flow properties of oils.

It is to be noted that, in this specification, the same substituent symbol (e.g. $R^1$) may be defined differently in respect of different compounds or components. The specification should therefore be read accordingly.

In a first aspect, the invention provides a chemical compound comprising or including a cyclic ring system, preferably an aromatic ring system, the compound carrying at least two substituents of the general formula (I) below on the ring system $$—A—NR^1R^2 \quad (I)$$

where A is an aliphatic hydrocarbyl group that is optionally interrupted by one or more hetero atoms (e.g. 0) and that is straight chain or branched, and $R^1$ and $R^2$ are the same or different and each is independently a hydrocarbyl group containing 9 to 40 carbon atoms, optionally interrupted by one or more hetero atoms, the substituents being the same or different and the compound optionally being in the form of a salt thereof. Preferably, A has from 1 to 20 carbon atoms and is preferably a methylene or polymethylene group.

"Hydrocarbyl" in this specification means an organic moiety composed of hydrogen and carbon which, unless the context states otherwise, may be aliphatic, including alicyclic; aromatic; or any combination thereof. It may be substituted or unsubstituted alkyl, aryl or aralkyl and may optionally contain unsaturation. Examples where it is substituted are oxy-, halogeno- and hydroxy-hydrocarbyl.

In a second aspect, the invention provides the use of a compound of the general formula (I) herein as an additive for improving the cold flow properties of a crude oil, lubricating oil or fuel oil.

In a third aspect, the invention provides a composition comprising an admixture of a major proportion of a crude oil, lubricating oil or fuel oil and a minor proportion of an additive comprising a compound of the general formula (I) herein.

In a fourth aspect, the invention provides a concentrate comprising an admixture of an additive comprising a compound of the general formula (I) herein and a carrier liquid therefor compatible with a crude oil, lubricating oil or fuel oil.

In tests to be described hereinafter, the chemical compounds of this invention are shown to have outstanding activity as flow improvers in exemplified oils.

The features of the invention will now be discussed in further detail.

CHEMICAL COMPOUNDS

The cyclic ring system may include homocyclic, heterocyclic, or fused polycyclic assemblies, or a system where two or more such cyclic assemblies are joined to one another and in which the cyclic assemblies may be the same or different. Where there are two or more such cyclic assemblies, the substituents of the general formula (I) may be on the same or different assemblies, preferably on the same assembly. Preferably, the or each cyclic assembly is aromatic, more preferably a benzene ring. Most preferably, the cyclic ring system is a single benzene ring when it is preferred that the substituents are in the ortho or meta positions, which benzene ring may be optionally further substituted.

The ring atoms in the cyclic assembly or. assemblies are preferably carbon atoms but may for example include one or more ring N, S or O atom, in which case or cases the compound is a heterocyclic compound.

Examples of such polycyclic assemblies include
  (a) condensed benzene structures such as naphthalene, anthracene, phenanthrene, and pyrene;
  (b) condensed ting structures where none of or not all of the rings are benzene such as azulene, indene, hydroindene, fluorene, and diphenylene;
  (c) rings joined "end-on" such as diphenyl;
  (d) heterocyclic compounds such as quinoline, indole, 2:3 dihydroindole, benzofuran, coumarin, isocoumarin, benzothiophen, carbazole and thiodiphenylamine;

(e) non-aromatic or partially saturated ring systems such as decalin (i.e. decahydronaphthalene), a-pinene, cardinene, and bornylene; and (f) three-dimensional structures such as norbornene, bicycloheptane (i.e. norbornane), bicyclooctane, and bicyclooctene.

Each hydrocarbyl group constituting $R^1$ and $R^2$ in the invention may for example be an alkyl or alkenyl group or a mono- or poly-alkoxyalkyl group. Preferably, each hydrocarbyl group is a straight chain alkyl group. The number of carbon atoms in each hydrocarbyl group is preferably 16 to 40, more preferably 16 to 24.

Also, it is preferred that the cyclic system is substituted with two only substituents of the general formula (I) and that A is a methylene group.

Examples of salts of the chemical compounds are the acetate and the hydrochloride.

The compounds may conveniently be made by reducing the corresponding amide which may be made by reacting a secondary amine with the appropriate acid chloride.

OIL

The oil may be a crude oil, i.e. oil obtained directly from drilling and before refining, the compounds of this invention being suitable for use as flow improvers or dewaxing aids therein.

The oil may be a lubricating oil which may be an animal, vegetable or mineral oil, such as petroleum oil fractions ranging from naphthas or spindle oil to SAE 30, 40 or 50 lubricating oil grades, castor oil, fish oils or oxidised mineral oil. Such an oil may contain additives depending on its intended use; examples are viscosity index improvers such as ethylene-propylene copolymers, succinic acid based dispersants, metal containing dispersant additives and zinc diaikyldithiophosphate antiwear additives. The compounds of this invention may be suitable for use in lubricating oils as flow improvers, pour point depressants or dewaxing aids.

The oil may be fuel oil suitably a middle distillate fuel oil. Such distillate fuel oils generally boil within the range of about 110° C. to about 500° C., e.g. 150° to about 400° C. The fuel oil can comprise atmospheric distillate or vacuum distillate, or cracked gas oil or a blend in any proportion of straight run and thermally and/or catalytically cracked distillates. The most common petroleum distillate fuels are kerosene, jet fuels, diesel fuels, heating oils and heavy fuel oils. The heating oil may be a straight atmospheric distillate, or it may contain minor amounts, e.g. up to 35 wt %, of vacuum gas oil or cracked gas oils or of both. The above-mentioned low temperature flow problem is most usually encountered with diesel fuels and with heating oils. The fuel oil may alternatively be a vegetable-based oil, e.g., linseed-based, either along or in admixture with a petroleum-based fuel.

The concentration of the additive in the oil may for example be 10 to 2,000 ppm of additive (active ingredient) by weight per weight of fuel, preferably 25 to 500 ppm, more preferably 100 to 200 ppm.

The additive should be soluble in the oil to the extent of at least 1000 ppm by weight per weight of oil at ambient temperature. However, at least some of the additive may come out of solution near the cloud point of the oil in order to modify the wax crystals that form.

CO-ADDITIVES

The additives of the invention may be used in combination with one or more co-additives for improving the cold flow properties of distillate fuels. Examples of such co-additives are as follows:

(i) Comb Polymers

Examples are those having the general formula where

D=R, CO.OR, OCO.R, $R^1$CO.OR or OR

E=H or $CH_3$ or D or $R^1$

G=H, or D m=1.0 (homopolymer) to 0.4 (mole ratio)

J=H, $R^1$, Aryl or Heterocyclic group, or $R^1$CO.OR

K=H, CO.$OR^1$, OCO. $R^1$, $OR^1$ or $CO_2H$

L=H, $R^1$, CO.$OR^1$, $OCO.R^1$, Aryl or $CO_2H$ n=0.0 to 0.6 (mole ratio)

$R \geq C_{10}$ $R^1 \geq C_1$

Another monomer may be terpolymerized if necessary.

Examples of suitable comb polymers are fumarate/vinyl acetate copolymers, particularly those described in European Patent Applications 0153176 and esterified olefin/maleic anhydride copolymers; polymers and copolymers of alpha olefin/maleic anhydride copolymers; polymers and copolymers of alpha olefins; esterified copolymers of styrene and maleic anhydride; and polymers of alkyl esters of itaconic acid or citaconic acid such as those where the alkyl groups have from 16 to 18 carbon atoms and the polymer has a number average molecular weight of from 1,000 to 20,000.

(ii) Polyoxyalkylene Compounds

Examples are polyoxyalkylene esters, ethers, ester/ethers and mixtures thereof, particularly those containing at least one, preferably at least two $C_{10}$ to $C_{30}$ linear saturated alkyl groups and a polyoxyalkylene glycol group of molecular weight 100 to 5,000 preferably 200 to 5,000, the alkyl group in said polyoxyalkylene glycol containing from 1 to 4 carbon atoms. These materials form the subject of European Patent Publication 0 061 895 A2. Other such additives are described in U.S. Pat. No. 4 491 455.

The preferred esters, ethers or ester/ethers which may be used may be structurally depicted by the formula where R and $R^2$ are the same or different and may be (a) n-alkyl

(b)

(c)

(d)

the alkyl group being linear and saturated and containing 10 to 30 carbon atoms, and A represents the polyalkylene segment of the glycol in which the alkylene group has 1 to 4 carbon atoms, such as polyoxymethylene, polyoxyethylene or polyoxytrimethylene moiety which is substantially linear; some degree of branching with lower alkyl side chains (such as in polyoxypropylene glycol) may be tolerated but it is preferred that the glycol should be substantially linear. A may also contain nitrogen.

Suitable glycols generally are substantially linear polyethylene glycols (PEG) and polypropylene glycols (PPG) having a molecular weight of about 100 to 5,000, preferably about 200 to 2,000. Esters are preferred and fatty acids containing from 10–30 carbon atoms are useful for reacting with the glycols to form the ester additives, it being preferred to use a $C_{18}$–$C_{24}$ fatty acid, especially behenic acid. The esters may also be prepared by esterifying polyethoxylated fatty acids or polyethoxylated alcohols.

Polyoxyalkylene diesters, diethers, ether/esters and mixtures thereof are suitable as additives, diesters being preferred for use in narrow boiling distillates when minor amounts of monoethers and monoesters (which are often formed in the manufacturing process) may also be present. It is important for additive performance that a major amount of the dialkyl compound is present. In particular, stearic or behenic diesters of polyethylene glycol, polypropylene glycol or polyethylene/polypropylene glycol mixtures are preferred.

Examples of other compounds in this general category are those described in Japanese Patent Publication Nos 2-51477 and 3-34790 (Sanyo).

(iii) Ethylene/Unsaturated Ester Copolymers

Examples are copolymers made by copolymerising ethylene with unsaturated monomers such as unsaturated mono and diesters of the general formula wherein $R^6$ is hydrogen or methyl, $R^5$ is a —$OOCR^8$ group wherein $R^8$ is a hydrogen formate or a $C_1$ to $C_{28}$, more usually $C_1$ to $C_{17}$, and preferably a $C_1$ to $C_8$, straight or branched chain alkyl group; or $R^5$ is a —$COOR^8$ group wherein $R_8$ is as previously described but is not hydrogen and $R^7$ is hydrogen or —$COOR^8$ as previously defined. The monomer, when $R^6$ and $R^7$ are hydrogen and $R^5$ is —$OOCR^8$, includes vinyl alcohol esters of $C_1$ to $C_{29}$, more usually $C_1$ to $C_5$, mono-carboxylic acid, and preferably $C_2$ to $C_{29}$, more usually $C_1$ to $C_5$ monocarboxylic acid, and preferably $C_2$ to $C_5$ monocarboxylic acid. Examples of vinyl esters which may be copolymerised with ethylene include vinyl acetate, vinyl propionate and vinyl butyrate or isobutyrate, vinyl acetate being preferred. We prefer that the copolymers contain from 5 to 40 wt % of the vinyl ester, more preferably from 10 to 35 wt % vinyl ester. There may also be mixtures of two copolymers such as those described in U.S. Pat. No. 3 961 91 6. It is preferred that these copolymers have a number average molecular weight as measured by vapour phase osmometry of 1,000 to 10,000, preferably 1,000 to 5,000.

(iv) Other Polar Compounds

Such other polar compounds are either ionic or non-ionic compounds which have the capability in fuels of acting as wax crystal growth inhibitors. Polar nitrogen containing compounds have been found to be especially effective when used in combination with the glycol esters, ethers or ester/ethers described above and such three component mixtures are within the scope of the present invention. These polar compounds are generally amine salts and/or amides formed by reaction of a least one molar proportion of hydrocarbyl substituted amines with a molar proportion of hydrocarbyl acid having 1 to 4 carboxylic acid groups of their anhydrides; ester/amides may also be used containing 30 to 300, preferably 50 to 150 total carbon atoms. These nitrogen compounds are described in U.S. Pat. No. 4 211 534. Suitable amines are usually long chain $C_{12}$–$C_{40}$ primary, secondary, tertiary or quaternary amines or mixtures thereof but shorter chain amines may be used provided the resulting nitrogen compound is oil soluble and therefore normally containing about 30 to 300 total carbon atoms. The nitrogen compound preferably contains at least one straight chain $C_8$ to $C_{40}$, preferably $C_{14}$ to $C_{24}$ alkyl segment.

Suitable amines include primary, secondary, tertiary or quaternary, but preferably are secondary. Tertiary and quaternary amines can only form amine salts. Examples of amines include tetradecyl amine, cocoamine, and hydrogenated tallow amine. Examples of secondary amines include dioctadecyl amine and methyl-behenyl. Amine mixtures are also suitable such as those derived from natural materials. A preferred amine is a secondary hydrogenated tallow amine of the formula $HNR^1R^2$ where in $R^1$ and $R^2$ am alkyl groups derived from hydrogenated tallow fat composed of approximately 4% $C_{14}$, 31% $C_{16}$, 59% $C_{18}$.

Examples of suitable carboxylic acids and their anhydrides for preparing the nitrogen compounds include cyclohexane, 1,2 dicarboxylic acid, cyclohexene 1,2 dicarboxylic acid, cyclopentane 1,2 dicarboxylic acid, naphthalene dicarboxylic acid and the like. Generally, these acids have about 5–13 carbon atoms in the cyclic moiety. Preferred acids useful in the present invention are benzene dicarboxylic acids such as phthalic acid, isophthalic acid, and terephthalic acid. Phthalic acid or its anhyddde is particularly preferred. The particularly preferred compound is the amide-amine salt formed by reacting 1 molar portion of phthalic anhydride with 2 molar portions of di-hydrogenated tallow amine. Another preferred compound is the diamide formed by dehydrating this amide-amine salt.

(v) Hydrocarbon Polymers

Examples are those represented by the following general formula where

T=H or $R^1$

U=H, T or Aryl v=1.0 to 0.0 (mole ratio)

w=0.0 to 1.0 (mole ratio)

where $R^1$ is alkyl.

These polymers may be made directly from ethylenically unsaturated monomers or indirectly by hydrogenating the polymer made from monomers such as isoprene, butadiene etc.

A particularly preferred hydrocarbon polymer is a copolymer of ethylene and propylene having an ethylene content preferably between 20 and 60% (w/w) and is commonly made via homogeneous catalysts.

(vi) Sulphur Carboxy Compounds

Examples are those described in EP-A-0261957 which describes the use of compounds of the general formula in which $-Y-R^2$ is $SO_3(-)(+)NR_3{}^3R^2$, $-SO_3(-)(+)HNR_2{}^3R^2$, $-SO_3(-)(+)H_2NR^3R^2$, $-SO_3(-)(+)H_2{}^3NR^2$, $-SO_2NR^3R^2$ or $-SO_3R^2$;

$-X-R^1$ is $-Y-R^2$ or $-CONR^3R^1$, $-CO_2(-)(+)NR_3{}^3R^1$, $-CO_2(-)(+)HNR_2{}^3R^1$, $-R_4-COOR_1$, $-NR^3COR^1$,

$-R^4OR^1$, $-R^4OCOR^1$, $-R^4$, $R^1$, $-N(COR^3)R^1$ or $Z(-)(+)NR_3{}^3R^1$;

$-Z(-)$ is $SO_3(-)$ or $-CO_2(-)$;

$R^1$ and $R^2$ are alkyl, alkoxy alkyl or polyalkoxy alkyl containing at least 10 carbon atoms in the main chain;

$R^3$ is hydrocarbyl and each $R^3$ may be the same or different and $R^4$ is nothing or is $C_1$ to $C_5$ alkylene and in the carbon-carbon (C—C) bond is either (a) ethylenically unsaturated when A and B may be alkyl, alkenyl or substituted hydrocarbyl groups or (b) part of a cyclic structure which may be aromatic, polynuclear aromatic or cycloaliphatic, it is preferred that $X-R^1$ and $Y-R^2$ between them contain at least three alkyl, alkoxyalkyl or polyalkoxyalkyl groups.

Multicomponent additive systems may be used and the ratios of additives to be used will depend on the fuel to be treated.

CONCENTRATE

The concentrates of the present invention are convenient as a means for incorporating the additive into bulk oil such as distillate fuel, which incorporation may be done by methods known in the art. The concentrates may also contain other additives as required and preferably contain from 3 to 75 wt %, more preferably 3 to 60 wt %, most preferably 10 to 50 wt % of the additives preferably in solution in oil. Examples of carrier liquid are organic solvents including hydrocarbon solvents, for example petroleum fractions such as naphtha, kerosene and heater oil; aromatic hydrocarbons such as benzene, xylene and toluene; and paraffinic hydrocarbons such as hexane and pentane. The carrier liquid must, of course, be selected having regard to its compatibility with the additive and with the fuel.

The additives of the invention may be incorporated into bulk oil by other methods such as those known in the art. If co-additives are required, they may be incorporated into the bulk oil at the same time as the additives of the invention or at a different time.

EXAMPLES

The invention will now be particularly described, by way of example only, as follows, where reference will be made to the accompanying drawings, the sole FIGURE of which is an NMR trace.

EXAMPLE 1

(i) Synthesis

The reaction scheme used was as follows:

Specifically, to 241 g (2 ME) of a $C_{20/22}$ mixed secondary amine in 500 ml toluene was added 72.5 ml (2.5 ME) of triethylamine followed, at 60° C., by 42.4 g (1 ME) of isophthaloyl dichloride in 100 ml toluene, the reaction temperature being maintained below 70° C. The mixture became rather viscous so a further 250 ml toluene was added. The resulting triethylamine hydrochloride was filtered off at about 70° C., and the flitrate evaporated to give 274 g of a diamide product.

To the above product in 500 ml THF at about 50° C. was added 266 ml (2.5 ME) 1M lithium aluminium hydride in THF and the mixture refluxed for 45 minutes. 20 ml water was then slowly added followed by 300 ml toluene. The mixture was warmed to 70° C. and filtered, and the precipitate washed with more hot toluene. The flitrate was then evaporated to give 247 g of the desired amine derivative.

DESCRIPTION OF THE DRAWINGS

Figure 1:
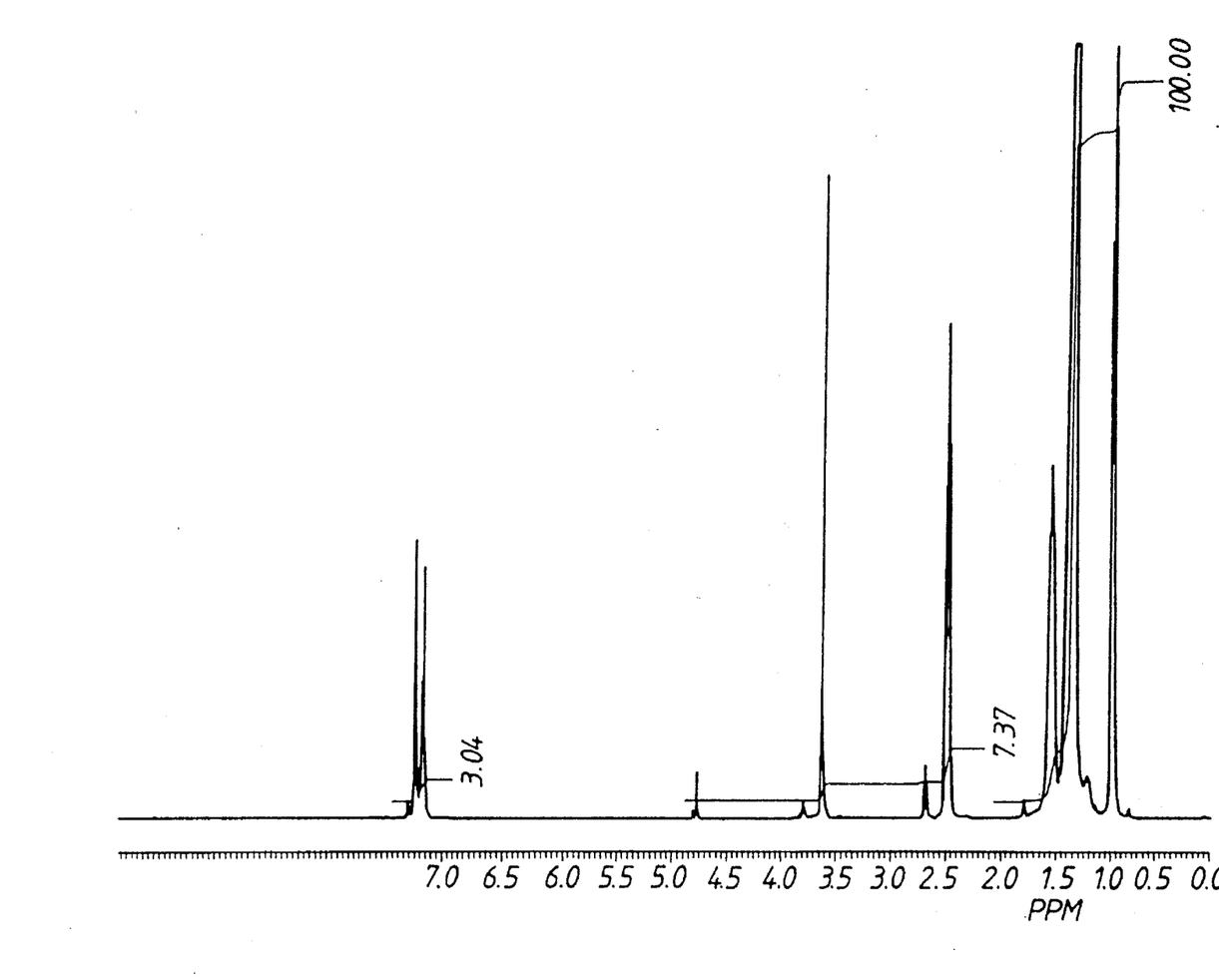

Referring to the accompanying figure, the peak at about 3.5 ppm on the NMR trace shows that there are methylene groups between a nitrogen atom and an aromatic ring, confirming the reduction of the carbonyl groups of the antide intermediate, and inclicating that the structure of the product is as depicted above. The peaks at 2.5 and 7.0 ppm indicate sidechain methylene groups adjacent to nitrogen, and aromatic hydrogens, respectively.

(ii) Testing

The effectiveness of the product of Example 1 in additive systems to improve filterability of distillate fuels was determined by the Flow Improver Extended Programme Cooling Test (XPCT) which is a slow cooling test designed to indicate whether the wax in the fuel will pass through filters such as those found in heating oil distribution system.

In the test, the cold flow properties of the described fuels containing the additives were determined as follows. 300 ml of fuel were cooled linearly at 1° C./hour to the test temperature and the temperature then held constant. Wax which had settled in the bottle was dispersed by gentle stirring, then a Cold Filter Plugging Point (CFPP) filter assembly, which is described in detail in "Journal of the Institute of Petroleum", Volume 52, Number 510, June 1966, pp. 173–285, inserted. The tap was opened to apply a vacuum of 500 mm of mercury and closed when 200 ml of fuel had passed through the filter into the graduated receiver. A PASS was recorded if the 200 ml passed through a given mesh size or a FAIL if the filter became blocked.

A series of CFPP filter assemblies with filter screens of different sizes including LTFT (AMS 100.65) and a Volkswagen Tank filter (part no KA/4-270/65.431-201-511) both intermediate between 30 and 40 μm were used to determine the finest mesh the fuel will pass. The sizes of the filter screens were as follows in order of increasing size, i.e. in order of decreasing severity as a test: 10 μ, 15 μ, 20 μ, 25 μ, 500, LTFT, 350, VW, 250, 200, 150, 120, 100, 80, 60, 40 and 30, where figures alone indicate mesh sizes.

(iii) Tests

The fuels used in the tests had the characteristics set forth in TABLE 1 below where the Initial (IBP), Final (FBP) and intermediate boiling point figures are in ° C. CP means "Cloud Point" and WAT means "Wax Appearance Temperature".

TABLE 1

| | Fuel Characteristics | | | | | | |
|---|---|---|---|---|---|---|---|
| | Fuel 1 | Fuel 2 | Fuel 3 | Fuel 4 | Fuel 5 | Fuel 6 | Fuel 7 |
| IBP | 174 | 181 | 135 | 140 | 157 | 135 | 140 |
| 5% | 198 | 202 | 187 | 185 | 187 | 187 | 188 |
| 10% | 210 | 216 | 196 | 195 | 203 | 199 | 198 |
| 20% | 225 | 228 | 208 | 208 | 221 | 210 | 208 |
| 30% | 244 | 244 | 222 | 222 | 244 | 222 | 221 |
| 40% | 262 | 259 | 238 | 238 | 260 | 236 | 235 |
| 50% | 277 | 273 | 256 | 255 | 277 | 250 | 251 |
| 60% | 292 | 288 | 274 | 275 | 293 | 265 | 269 |
| 70% | 308 | 304 | 293 | 296 | 310 | 282 | 288 |
| 80% | 324 | 321 | 314 | 317 | 329 | 302 | 310 |
| 90% | 344 | 343 | 342 | 340 | 354 | 325 | 334 |
| 95% | 358 | 358 | 360 | 354 | 374 | 340 | 351 |
| FBP | 375 | 377 | 375 | 365 | 390 | 359 | 360 |
| CP | +4° C. | +3° C. | +5° C. | −1° C. | +3° C. | −5° C. | −3° C. |
| WAT | +3.6° C. | +1.7° C. | +4.7° C. | −1.5° C. | +2.3° C. | −3.3° C. | |
| Wax, 10° below CP | 3.1% | 2.0% | 2.4% | 2.2% | 1.8% | 2.3% | 2.4% |

The additive combinations used comprised the following additive components:

A: the product of the above synthesis.

B: a mixture of two ethylene/vinyl acetate copolymers comprising 13 parts by weight a first copolymer and 1 part by weight of a second and different copolymer.

C: an amide-amine salt, namely the N,N-dialkylammonium salt of 2-$N^1N^1$-dialkylamidobenzoate wherein each alkyl group contains 16 and 18 carbon atoms and made by reacting one mole of phthalic anhydride with two moles of dihydrogenated tallow amine.

D: a homopolymer of an ester of itaconic acid having linear alkyl groups of 16 carbon atoms made by polymerising the monomer using a free radical catalyst, the homopolymer having an $M_w$ of 4000.

E: a homopolymer of an ester of itaconic acid having linear alkyl groups of 18 carbon atoms made by polymerising the monomer using a free radical catalyst, the homopolymer having an $M_w$ of 4000.

The tests were carried out on untreated fuel, on fuel treated with 400 ppm of an additive combination (100A:100B:100C:50D:50E), and on fuel treated with 800 ppm of an additive combination (200A:200B:200C:100D:100E).

Tests were also carried out, by way of comparison only, on fuel treated with 800 ppm of a combination comprising 200B:300C:150D:150E.

The above figures indicate the concentration of the particular component they precede in ppm.

(iv) Results

The results are shown in Table 2 below.

TABLE 2

| | Tested at −14° C. | |
|---|---|---|
| Fuel | Treat Rate (ppm) | XPCT |
| 1 | 0 | 40# |
| | 400 | 100# |
| | 800 | 15μ |
| 2 | 0 | 120# |
| | 400 | 500# |

TABLE 2-continued

| | Tested at −14° C. | |
|---|---|---|
| Fuel | Treat Rate (ppm) | XPCT |
| | 800 | 10μ |

TABLE 2-continued

| | Tested at −14° C. | |
|---|---|---|
| Fuel | Treat Rate (ppm) | XPCT |
| 3 | 0 | 60# |
| | 400 | 150# |
| | 800 | 15μ |
| 4 | 0 | 40# |
| | 400 | 200# |
| | 800 | 10μ |
| 5 | 0 | 150# |
| | 400 | 15μ |
| | 800 | 15μ |
| 6 | 0 | 100# |
| | 400 | LTFT |
| | 800 | 15μ |
| 7 | 0 | >30# |
| | 400 | VW |
| | 800 | 10μ |
| | 800 | 500# |
| | (comparison) | |

The result of the comparison test is the last result in the table as indicated and shows the value of including additive component A.

EXAMPLES 2–11

The above tests were also carried out on a fuel that had been pre-treated with 50 ppm of a commercially available ethylene/vinyl acetate copolymer to give a base XPCT pass of 80#. The characteristics of the fuel were:

| | |
|---|---|
| IBP | 145.0° C. |
| FBP | 366.6° C. |
| CP | −5° C. |
| WAT | −6.2° C. |
| Wax | 1.64% |
| (at 10° C. below C.P) | |

Compounds of the invention were treated for XPCT at various treat rates and when carrying alkyl groups of various numbers of carbon atoms. The results are summarised in Table 3 and Table 4 below.

TABLE 3

| Compound | Treat Rate (ppm) | R 16/18 mix | 18/18 | 18/20 | 18/22 | 20/22 mix | 22/22 |
|---|---|---|---|---|---|---|---|
| [ortho-bis(CH$_2$NR$^1$R$^2$)benzene] | 50 | — | 150# | 120# | VW | 500# | 25μ |
| | 125 | 150# | VW | VW | LTFT | 15μ | 20μ |
| | 250 | 200# | VW | LTFT | 500# | 15μ | VW |
| [ortho-bis(CH$_2$NR$^1$R$^2$)benzene] | 50 | — | — | — | — | 20μ | — |
| | 125 | — | — | — | — | 15μ | — |
| | 250 | 120# | — | — | — | 20μ | — |
| [para-bis(CH$_2$NR$^1$R$^2$)benzene] | 50 | — | — | 100# | VW | 150# | — |
| | 125 | — | — | VW | 500# | VW | — |
| | 250 | — | — | 350# | 20μ | 120# | — |
| | 500 | — | — | 500# | 15μ | | — |
| [dimethyl-bis(CH$_2$NR$^1$R$^2$)benzene] | 25 | — | — | — | — | — | LTFT |
| | 50 | — | — | — | — | 500# | 500# |
| | 125 | — | — | — | — | 20μ | 20μ |
| | 250 | — | — | — | — | 500# | 20μ |
| [trimethyl-tris(CH$_2$NR$^1$R$^2$)benzene] | 25 | — | — | — | — | — | LTFT |
| | 50 | — | — | — | — | — | 500# |
| | 125 | — | — | — | — | — | 15μ |
| | 250 | — | — | — | — | — | 15μ |

TABLE 3-continued

| Compound | Treat Rate (ppm) | 16/18 mix | 18/18 | 18/20 | 18/22 | 20/22 mix | 22/22 |
|---|---|---|---|---|---|---|---|
|  | 25 | — | — | — | — | — | — |
| | 50 | — | — | — | — | VW | — |
| | 125 | — | — | — | — | 20μ | — |
| | 250 | — | — | — | — | 15μ | — |
|  | 50 | 120# | 120# | — | 500# | 150# | — |
| | 125 | 150# | VW | — | 15μ | VW | — |
| | 250 | 200# | 500# | — | 20μ | VW | — |
|  | 25 | — | — | — | — | 150# | — |
| | 50 | — | — | — | — | 150# | — |
| | 125 | — | — | — | — | 120# | — |
| | 250 | — | — | — | — | 80# | — |

TABLE 4

| Compound | Treat Rate (ppm) | 10 | 12 | 14 | 16 | 18 | 18–22 mix |
|---|---|---|---|---|---|---|---|
|  | 50 | 150# | 150# | 120# | 80# | LTFT | 120# |
| | 125 | 150# | 150# | 350# | VW | 350# | 120# |
| | 250 | 150# | 150# | VW | VW | LTFT | 150# |
|  | 50 | 100# | — | — | — | 150# | 100# |
| | 125 | 80# | 150# | 80# | 80# | 150# | 120# |
| | 250 | 80# | 150# | 150# | 80# | 350# | VW |
| | 500 | — | 100# | 100# | 80# | — | — |

The presence of methyl substituents in the above formulae is indicated by unconnected bond lines. In the table, a dash means that no measurement was made.

We claim:

1. A crude oil, lubricating oil or fuel oil composition exhibiting improved cold flow properties consisting essentially of said oil and a flow improvement additive in an amount of 10 to 2,000 ppm of the oil, the additive being a chemical compound having a cyclic ring system, the compound carrying at least two substituents of the general formula (I) below on the ring system $$-A-NR^1R^2 \qquad (I)$$

where A is an aliphatic hydrocarbylene group that is optionally interrupted by one or more hetero atoms and is straight chain or branched, and $R^1$ and $R^2$ are the same or different and each is independently a hydrocarbyl group containing 9 to 40 carbon atoms optionally interrupted by one or more hetero atoms, the substituents being the same or different and the compound optionally being in the form of a salt thereof, subject to the provisos that the ring system is not an alkyl-substituted phenol, that when it is dimethylbenzene $R^1$ and $R^2$ contain at least 16 carbon atoms, and that when $R^1$ and $R^2$ of one substituent are both alkyl, $R^1$ and $R^2$ of the or each remaining substituent are not both interrupted and substituted alkyl or interrupted and substituted aralkyl groups.

2. The composition of claim 1 wherein A has from 1 to 20 carbon atoms.

3. The compositon of claim 2 wherein A is a methylene or polymethylene group.

4. The composition of any of the preceding claims wherein the cyclic ring system is an aromatic ring system.

5. The composition of claim 4 wherein the ring system is a benzene ring.

6. The composition of any of the preceding claims wherein the system is substituted with only two substituents of the general formula (I), and A is a methylene group.

7. The composition of on claim 5 wherein the substituents are in the ortho or meta positions with respect to one another in the benzene ring.

8. The composition of claim 1 wherein each of $R^1$ and $R^2$ is a straight chain alkyl group.

9. The composition of claim 8 wherein each of $R^1$ and $R^2$ has from 16 to 40 carbon atoms.

10. The composition of claim 9 wherein each of $R^1$ and $R^2$ has from 16 to 24 carbon atoms.

11. A composition as claimed in claim 1 wherein $R^1$ and $R^2$ each represent a mono- or poly-alkoxyalkyl group.

12. A composition as claimed in claim 1, wherein the ring system is a dimethyl or trimethyl benzene ring and $R^1$ and $R^2$ each represent a hydrocarbyl group containing from 16 to 40 carbon atoms.

13. The composition of claim 1 wherein the oil is a middle distillate fuel boiling in the range of 110° C. to 500° C.

14. The composition of claim 13 wherein the additive is present in the fuel at a concentration within the range of 25 ppm to 500 ppm weight of active ingredient per weight of fuel.

15. The composition of claim 14 wherein the range is 100 ppm 200 ppm.

16. The composition of any one of claims 13 to 15 wherein the additive is in combination with one or more other additives for improving the cold flow properties of distillate fuels.

17. The composition of claim 16 wherein the other additive or one of the other additives is a N,N-dialkylammonium salt of 2-N'N'-dialkylamidobenzoate.

* * * * *

UNITED STATES PATENT AND TRADEMARK OFFICE
CERTIFICATE OF CORRECTION

PATENT NO. : 5,516,443
DATED : May 14, 1996
INVENTOR(S) : G. Jackson and R.E.M. Kenward It is certified that error appears in the above-indentified patent and that said Letters Patent is hereby corrected as shown below:

Column 15,

In claim 1, line 16, delete the terms "or each".

In claim 7, line 31, delete "on".

Signed and Sealed this

Thirteenth Day of August, 1996

Attest:

BRUCE LEHMAN

*Attesting Officer*         *Commissioner of Patents and Trademarks*